(12) United States Patent  
Parnagian

(10) Patent No.: US 8,333,707 B2
(45) Date of Patent: Dec. 18, 2012

(54) PATIENT MONITOR WITH FLUID PORT PROTECTION

(75) Inventor: Edward Parnagian, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1895 days.

(21) Appl. No.: 10/934,712

(22) Filed: Sep. 3, 2004

(65) Prior Publication Data

US 2006/0052718 A1   Mar. 9, 2006

(51) Int. Cl.
*A61B 5/00* (2006.01)

(52) U.S. Cl. .......................................... 600/529; 600/532

(58) Field of Classification Search .................. 600/529; 235/381; 174/67, 66; 439/137, 34, 139; 96/4; 250/343, 504 R; 128/204.25, 200.24, 128/207.14; 482/13; 73/23.3
See application file for complete search history.

(56) References Cited

U.S. PATENT DOCUMENTS

| | | | | |
|---|---|---|---|---|
| 2,484,217 A * | 10/1949 | Gardenier | ................. | 600/532 |
| 4,640,564 A * | 2/1987 | Hill | .................. | 439/137 |
| 4,765,193 A * | 8/1988 | Holden et al. | ................ | 73/865.9 |
| 4,774,384 A * | 9/1988 | Gregory | ................. | 174/67 |
| 4,793,818 A * | 12/1988 | Poirier | ................. | 439/140 |
| 5,212,347 A * | 5/1993 | Powers et al. | ................. | 174/67 |
| 5,277,195 A * | 1/1994 | Williams | ................. | 600/538 |
| 5,464,983 A * | 11/1995 | Wang | ................. | 250/343 |
| 5,873,361 A * | 2/1999 | Hakala | ................. | 128/204.23 |
| 5,932,845 A * | 8/1999 | Lacy | ................. | 174/67 |
| 6,039,696 A * | 3/2000 | Bell | ................. | 600/532 |
| 6,193,864 B1 * | 2/2001 | Leader et al. | ................. | 204/403.02 |
| 6,208,264 B1 * | 3/2001 | Bradney et al. | ................. | 340/5.2 |
| 2004/0089155 A1 * | 5/2004 | Larsen et al. | ................. | 96/4 |

* cited by examiner

*Primary Examiner* — Patricia Mallari
(74) *Attorney, Agent, or Firm* — W. Brinton Yorks, Jr.

(57) ABSTRACT

A patient monitoring instrument protects the ports of a patient gas analyzer when not in use. A spring-loaded door covers the inlet and outlet ports of the gas analyzer when not connected to a gas collection tube. The door can be opened against the force of its spring with a gas tube connector, which is guided into its fitting by the contour of the door. When the connector is locked in place the connector holds the door open, exposing the outlet port of the analyzer.

13 Claims, 5 Drawing Sheets

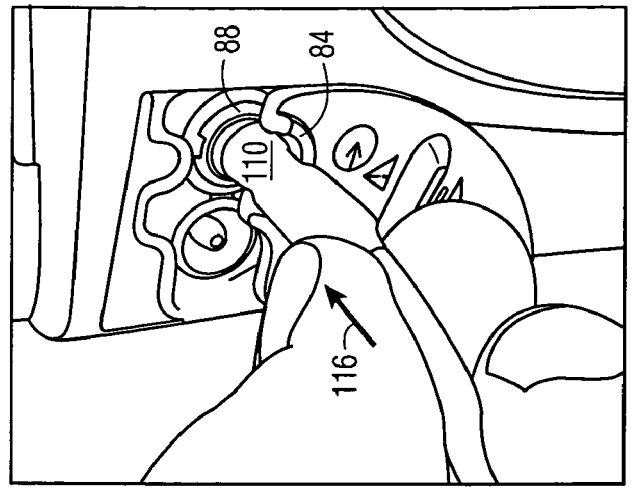
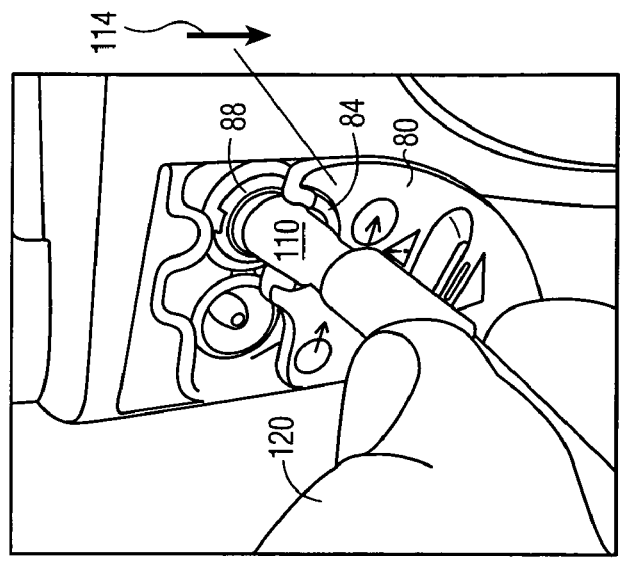
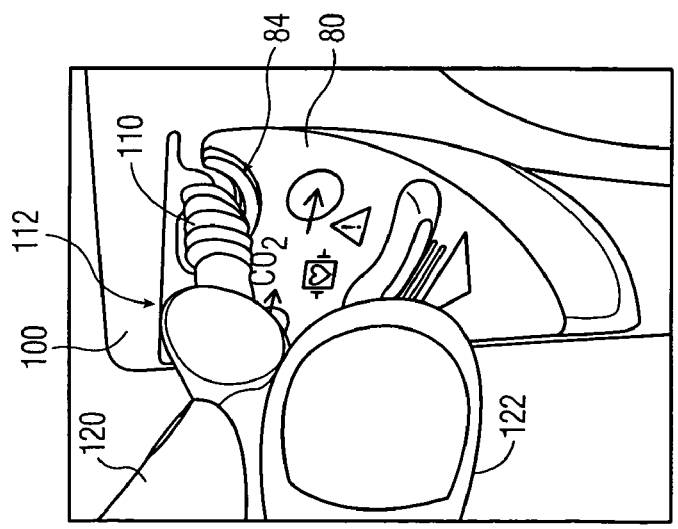

PATIENT MONITOR WITH FLUID PORT PROTECTION

This invention relates to medical patient monitoring instruments and, in particular, to patient monitoring instruments which protect gas ports from contamination and blockage.

Patient monitors are in widespread use in hospitals and by emergency medical personnel for monitoring the vital signs of patients. In the past these monitors have been of substantial size and weight and employed a cathode ray tube monitor to display patient vital signs such as heartbeat, respiration, blood oxygen, and other parameters of bodily functions. Today these monitors are becoming smaller and lighter and, in many instances, are designed for portability. This portability enables the monitors to be used in their conventional settings in emergency rooms and intensive care units, and also enables them to be hung on a bedrail as a patient is moved from one location in a hospital to another. It also enables the monitors to be used in ambulances and other emergency vehicles, and even to be used at the site of an accident or other medical emergency. A portable monitor can even be placed in use out-of-doors, enabling emergency personnel to immediately begin monitoring a patient's vital signs and administering life-saving treatments afforded by the instrument.

One of the patient vital signs conventionally monitored by a patient monitor is end tidal $CO_2$ ($EtCO_2$). In this application a gas sampling line is fitted to the patient's respiratory system and the connector end of the gas sample collection tube is connected to the $CO_2$ inlet of the monitor. A low pressure sampling pump draws the patient's breath into the patient monitor where it is analyzed and expelled through an outlet port. The results of the analysis are typically shown graphically or numerically on the display of the monitor.

The patient monitors in common use in hospitals generally leave the gas inlet and outlet ports for gas sampling unprotected, as there is generally little risk of contamination or blockage of the ports in the hospital setting. One commercially available capnography monitor does have a door which closes over the gas inlet port located on the top of the monitor. To access the inlet port the user must open the hinged door with one hand and insert and lock the collection tube connector with the other hand. However a portable patient monitor which is taken to accident sites by emergency medical personnel should be easier to operate. The collection tube should be connectable to the patient monitor with one hand, and should be possible by touch alone, as the medical technician is often directing his or her visual attention to an injured patient. Furthermore, such patient monitors are often used outdoors at an accident site such as alongside a highway. The inlet and outlet ports can readily become contaminated with blowing dust and other particulate matter from passing automobiles and should be protected against such hazards, but not in a way which significantly impedes the quick and simple connection of the gas line.

In accordance with the principles of the present invention, the gas inlet and outlet ports of a patient monitoring instrument are both protected from contamination when not in use. A spring-loaded door covers the unused ports and can be easily opened with the connector end of a gas sample collection tube. A guide on the door which can be located tactilely aids in both opening the door and guiding the collection tube connector to the mating connector on the monitor. When the sample collection tube connector is connected to the gas inlet the connected tube holds the door open and exposes the outlet port. The sample collection tube can be easily connected with only one hand by touch alone.

In the drawings:

FIGS. 5a-5e illustrate the connection of a gas line connector to a gas inlet of a patient monitor of the present invention.

Figure 1:
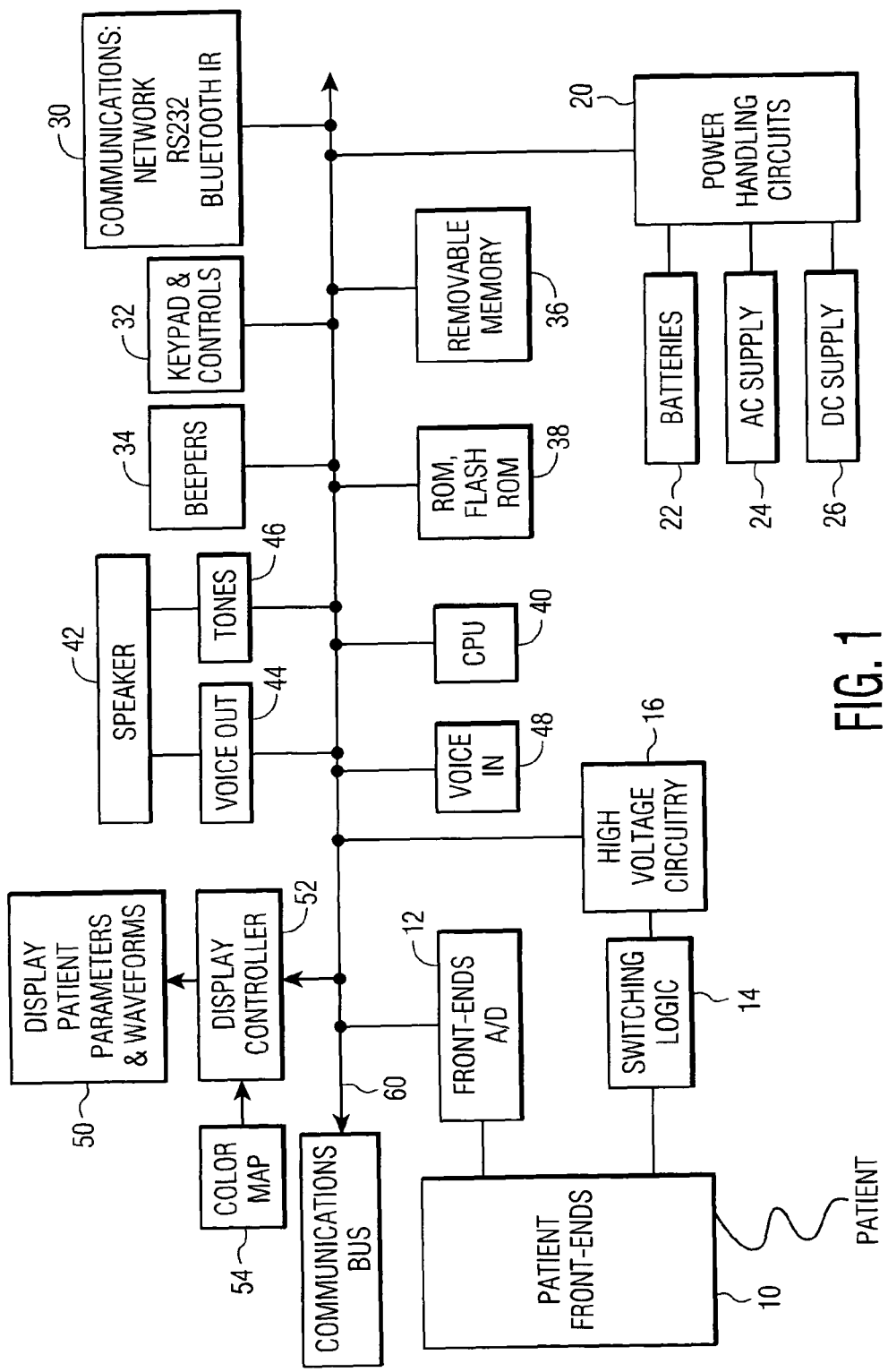
FIG. 1 illustrates in block diagram form a portable patient monitoring instrument constructed in accordance with the principles of the present invention.

Referring first to FIG. 1, a patient monitoring instrument constructed in accordance with the principles of the present invention is shown in block diagram form. The monitor shown in FIG. 1 is capable of performing end tidal $CO_2$ monitoring of a patient as well as other patient monitoring and treatment tasks. The monitor is capable of performing ECG monitoring including the cardiac monitoring necessary for automatic defibrillation decision-making. The illustrated monitor is also capable of $SpO_2$ oxygen sensing and noninvasive blood pressure monitoring. Other functions such as invasive blood pressure monitoring and patient temperature monitoring may also be found in such a multi-functional monitor. The monitor has a plurality of patient front-ends 10, which are input circuitry for the sensors attached to the patient. This circuitry includes conventional sensing and amplification circuitry for ECG electrodes, for optical oxygen sensors, for pressure sensing and for carbon dioxide measurement, among others. The information received by the patient sensors and processed by the front-end circuitry 10 is digitized by front-end A/D converters 12. The digitized information is coupled to processing circuitry of the monitor by a communications bus 60 which connects data between the various modules of the monitor.

The monitor includes high voltage circuitry 16 for defibrillator operation. The high voltage circuitry produces the high voltage pulse necessary for defibrillation which is connected at the appropriate time by switching logic 14 to defibrillator electrodes coupled to the patient. This circuitry provides the high voltage shock needed to disrupt the heart from ventricular fibrillation. The shock level and waveform delivered for defibrillation can be automatically calculated by a processor in the monitor or can be manually set by an experienced medical technician or physician.

Power for the modules of the monitor is distributed by power handling circuits 20. The power handling circuits 20 will distribute power from batteries 22, from an a.c. supply 24, or from a DC supply 26. The a.c. and DC supplies are also coupled to circuitry which charges the batteries when the monitor is powered from these sources.

The information obtained by the monitor may be sent to other instruments or locations by communications circuitry 30. This may include a network connection, an RS232 connection, Bluetooth or infrared wireless connections.

The monitor is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor is operated under control of a central processing unit (CPU) 40. The CPU runs software stored on a read-only memory (ROM) 38. Flash ROM is also provided for the control of feature setups and new or special capabilities such as waveform information. Removable memory 36 is provided for storage of recorded information during a patient event such as ventricular fibrillation. Patient information such as cardiac waveforms before and after defibrillation are stored on the removable memory 36, which can be removed and given to a subsequent care-giver for review, record-keeping, and subsequent diagnosis. The removable memory 36 can also record voice information from a care-giver speaking into a microphone 48.

Beepers 34 are provided which produce sounds during certain monitoring functions such as a beep in response to each heart cycle. The beepers can also be used to issue audible alerts and alarms which a patient medical crisis is detected. Other audible information is provided by a loudspeaker 42. The loudspeaker 42 can reproduce pre-recorded voice instructions and information stored and reproduced from voice out circuitry 44. The loudspeaker can also reproduce tones 46 during operation of the keypad and other controls.

A display 50 is provided for the display of patient parameters, waveforms, and other patient data acquired by the monitor. The information to be displayed is provided to a display controller 52 which provides the necessary drive signals for display of the information on the display. In a constructed embodiment the display is a color LCD display, although other types of displays such as a CRT display may be used in a particular embodiment. The display controller 52 displays information in accordance with a color map provided by color map store 54. In a constructed embodiment the color map is stored in tabular form. In other embodiments the color map may be stored as an algorithm or other programmed information. In the constructed embodiment the display information is coupled to the display 50 with a color code by which the display controller selects the pixels for display of the desired information and background colors.

Figure 2:
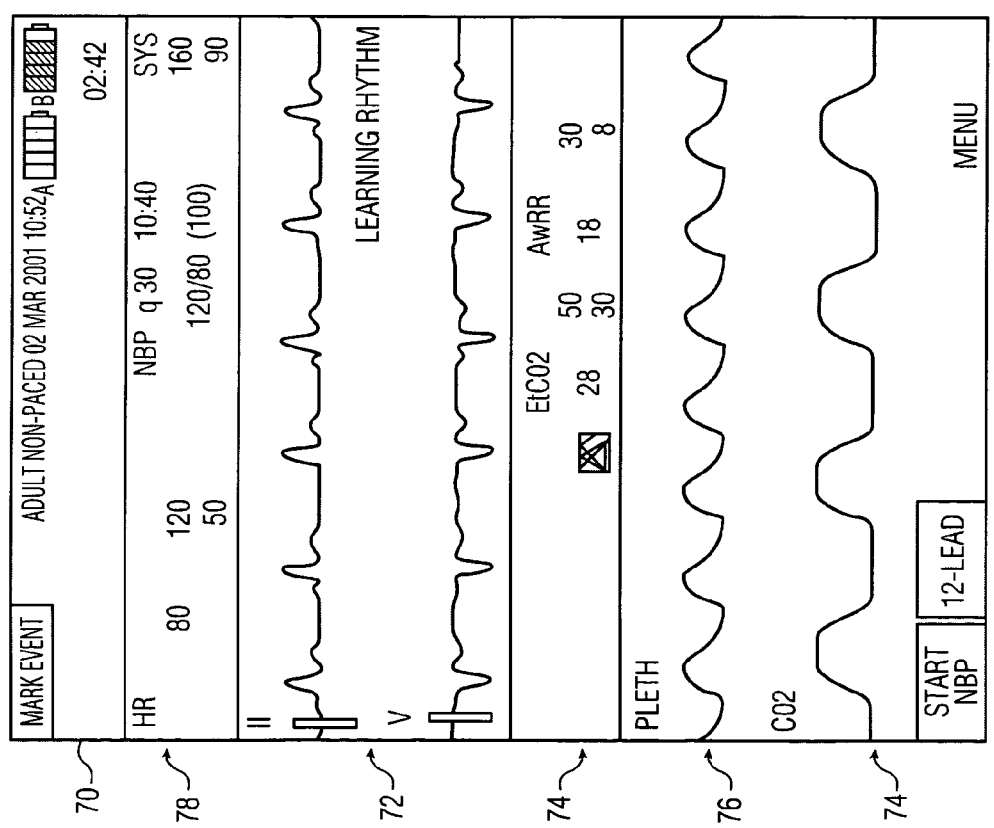
FIG. 2 illustrates a typical patient monitor display.

FIG. 2 illustrates a typical display 70 of a monitor constructed in accordance with the principles of the present invention. Under normal room lighting conditions the background of the display 70 is black or gray as indicated by reference numeral 78. The graphical information at the very top of the display 70 is displayed in white which contrasts sharply against the black background. To readily distinguish and associate the different types of information displayed, the numerical and graphical information is displayed in color. For instance the numerical heart rate 80 and the heart traces below as indicated at 72 are displayed in green. The numerical $CO_2$ reading of 28 and the $CO_2$ trace indicated at 74 are displayed in light blue. The plethysmograph trace 76 is displayed in purple.

Figure 3:
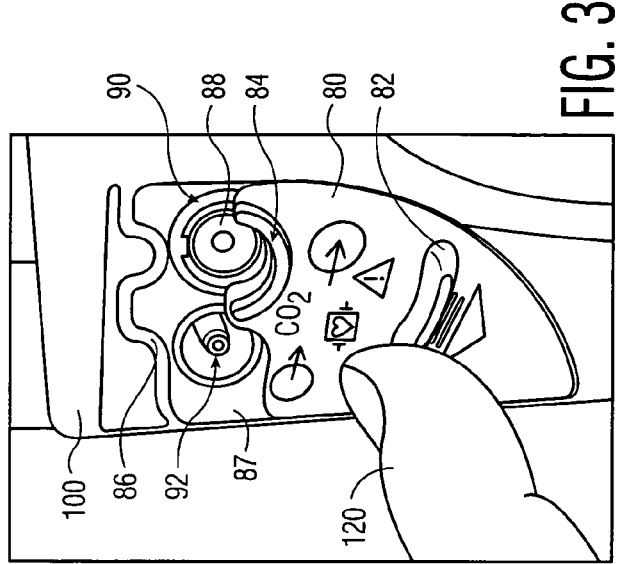
FIG. 3 illustrates a spring-loaded gas port door of the present invention being held in the open position.

In accordance with the principles of the present invention a patient monitoring instrument is equipped with a door which protects both the inlet and outlet ports for the $CO_2$ lines. FIG. 3 illustrates a spring-loaded door 80 of a patient monitor being held in the open position by a user's thumb 120. The door 80 is located on the left side of the case 100 of the patient monitor. Located on a recessed panel 87 behind the spring-loaded door 80 are a $CO_2$ inlet port 90 and a $CO_2$ exhaust port 92. In this particular embodiment the exhaust port 92 includes a projecting tubing adapter. The inlet port 90 includes a luer receptacle 88 which mates with the connector on a gas sample collection tube. The door 80 is being held open against the force of its spring by the thumb 120 which is pressing downward against a projection 82 on the front of the door. If the user's thumb were withdrawn from the projection 82 on the front of the door 80, the door would spring upward and the contoured upper edge of the door would align with the correspondingly shaped molding 86 at the top of the recessed panel 87. The door 80 would stay in that position by reason of the force of its spring. Also formed on the upper edge of the door 80 is a semi-circular alignment ramp 84. As will be seen below, this alignment ramp 84 enables the door 80 to be opened with a collection tube luer held in one hand of a user.

The alignment ramp can be located on the front of the door by touch alone and also serves to guide the collection tube luer to the luer receptacle 88 of the inlet port 90.

Figure 4C:
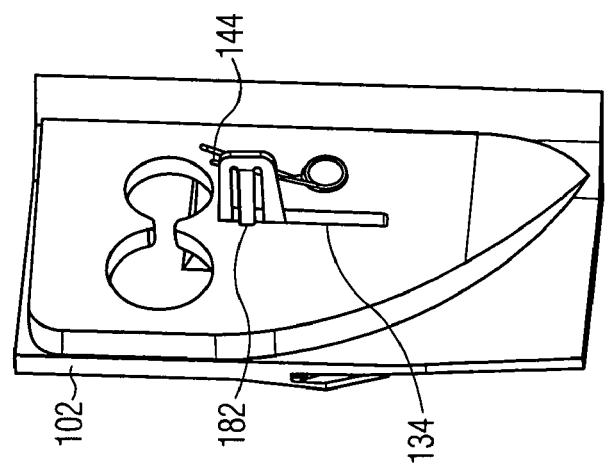
FIGS. 4a-4c illustrate components of the spring-loaded door mechanism of FIG. 3.
Figure 4B:
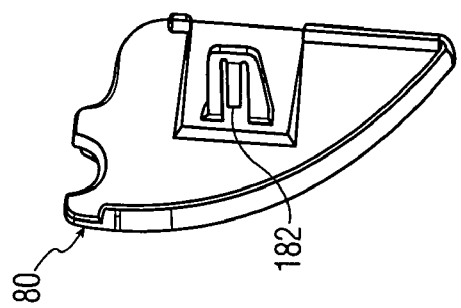
Figure 4A:
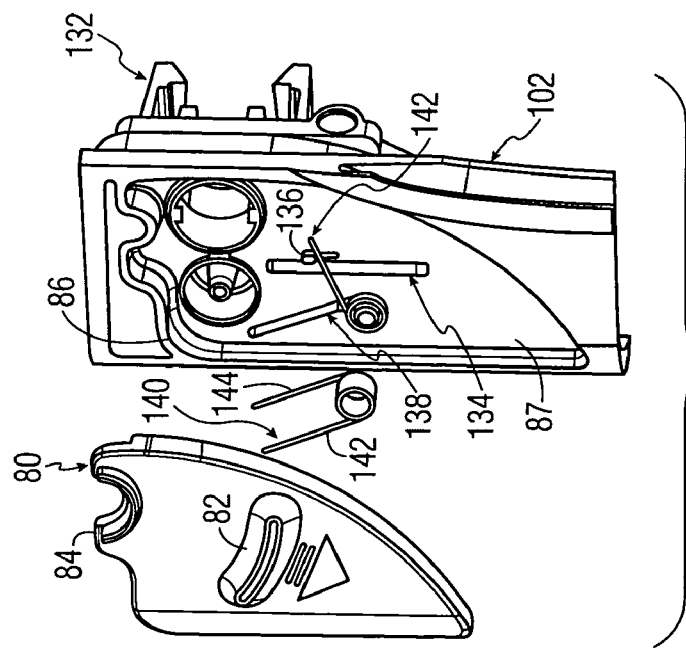

The $CO_2$ door and spring mechanism of FIG. 3 is shown in greater detail in FIGS. 4a-4c. FIG. 4a is an exploded view of the case segment 102 which contains the gas port recessed panel 87 for the spring-loaded door 80. A spring 140 is shown in its pre-assembled position and in its seated position in a spring recess 138 in the recessed panel 87. When the spring 140 is seated its outer leg 142 is rotated clockwise and positioned behind a post 136 which projects from the recessed panel. The coiled body of the spring and the inner spring leg 144 are seated in the spring recess 138. The installed spring 140 is seen to traverse a door retaining slot 134 in the recessed panel. When the spring 140 is set in this manner the spring will exert a pre-determined load on the installed door which is necessary for smooth operation of the spring-loaded door.

FIG. 4b is a view of the rear of the door 80 which shows a door retaining snap 182 projecting from the rear of the door. The door 80 is assembled in the recessed panel 87 by pushing the retaining snap 182 through the door retaining slot 134 until the center leg of the retaining snap springs laterally to hold the door in place, as shown in FIG. 4c, to prevent the door from separating from the case segment 102 while still being free to slide up and down in the retaining slot 134. When the door 80 is installed in this manner the outer leg 142 will bear upward against the bottom of the retaining snap to spring-load the door. FIG. 4c is a view of the installed door 80 and spring 140 from the inside of the case segment 102. Not shown in this view for reasons of clarity but partially visible in FIG. 4a is a holder 132 on the back of the case segment 102. The holder 132 is bonded to the case segment 102 by double-sided adhesive. The holder also serves to hold a luer receptacle (discussed below) in place behind the inlet port 90 and to lock the inner leg 144 of the spring in its pre-loaded position.

Figure 5D:
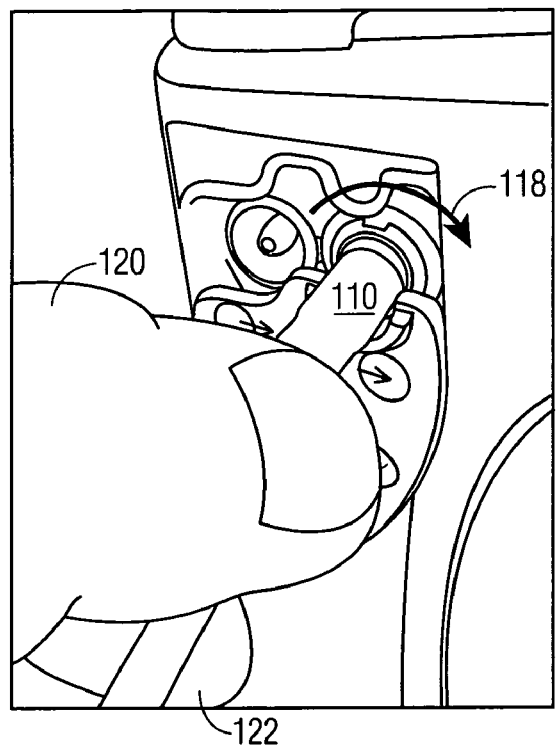
Figure 5E:
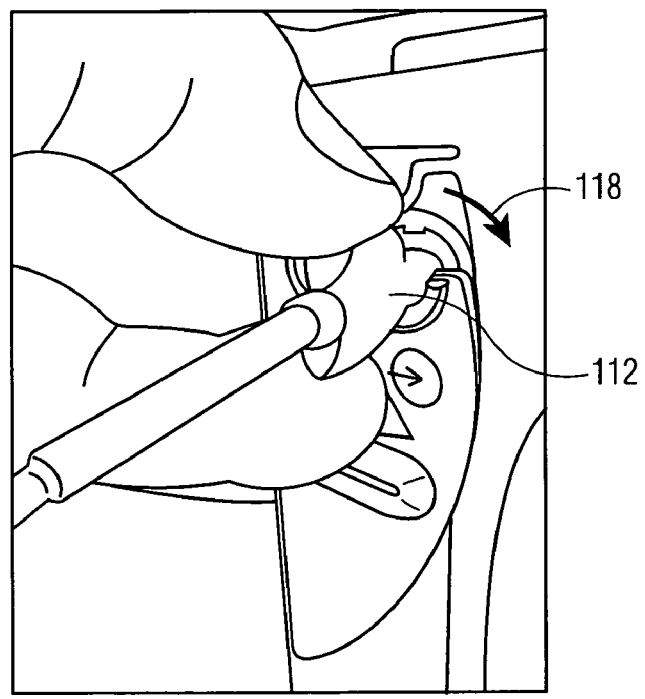

FIGS. 5a-5e illustrate how the $CO_2$ port door of FIG. 3 can be easily opened with one hand and a $CO_2$ line connector connected to the $CO_2$ inlet port. FIG. 5a shows the end of a $CO_2$ collection tube held between the thumb 120 and finger 122 of a user. At the distal end of the collection tube is a connection luer fitting 110. Just before the fitting 110 is a winged portion 112 of the connector which is used to lock the luer fitting in place. In the illustration of FIG. 5a the end of the luer fitting 110 is placed against the surface of the monitor case 100, just above the alignment ramp 84 at the top of the door 80. This positioning of the luer fitting can be easily attained by visually observing the alignment ramp 84 at the top of the door 80, or by tactilely feeling the projecting alignment ramp and placing the luer fitting 110 just above it. Thus, this position can be attained without the need to visually observe the alignment ramp 84 when placing the luer fitting 110 against the monitor.

In FIG. 5b the user has pressed downward with the luer fitting 110 against the alignment ramp 84, as indicated by the arrow 114. This motion opens the door 80 against the force of its spring, revealing the previously protected $CO_2$ inlet and outlet ports. When the user has pressed the door 80 downward as far as it goes the luer fitting is held in alignment with the luer receptacle 88 of the $CO_2$ inlet port 90 by virtue of the curvature of the alignment ramp 84.

With the luer fitting 110 thus aligned with the luer receptacle 88, the user pushes the luer fitting into its mating receptacle as shown in FIG. 5c. The arrow 116 illustrates the direction of the motion of the user's hand which causes the luer fitting 110 to engage the luer receptacle 88. When the luer fitting 110 is engaged with the receptacle the user can roll the tube between his thumb 120 and finger 122 in the direction indicated by arrow 118 in FIG. 5d to lock the connector in place. As a final check that the luer is locked in place, the user can apply a small amount of torque to the connector by means of the winged portion 112, as indicated by the arrow 119 in FIG. 5e. The $CO_2$ sample collection tube is now securely connected to the inlet of the $CO_2$ monitor, and the engaged connector 110 holds the door 80 in its open position so that gases can freely exit the system by way of the exposed $CO_2$ outlet port 92. As the illustrations show, a user can engage the collection tube in its port on the monitor with one hand and can do so by touch, without the need to visually observe the $CO_2$ port door during the process.

When the connector of the gas collection tube is retracted from the inlet port 90, the door 80 springs shut, resuming its protection of both the inlet and outlet ports 90, 92 of the patient monitor.

It will be recognized that two hands can be used to open the protecting door 80 and engage the collection tube connection, as in the prior art. The user can use a thumb or finger to press down on the projection 82 on the door 80 to open the door with one hand, then engage the inlet port with the connector of a collection tube held in the other hand. However it is anticipated that users will soon prefer the one-handed technique described above, particularly in emergency situations.

What is claimed is:

1. A patient monitoring instrument, comprising:
   a case;
   an opening in the case forming a first port;
   a door mounted on the outside of the case and having an edge extending around the entire periphery of the door, the door being mounted so that it is moveable between at least first and second positions, the door covering the first port in the first position and uncovering the first port in the second position;
   a spring resiliently biasing the door to the first position; and
   a concave contour formed on the edge of the door at a location that is positioned adjacent the first port when the door is in the second position, the contour being positioned so that it partially surrounds the first port when the door is in the second position.

2. The patient monitoring instrument of claim 1, wherein the patient monitoring instrument further comprises a portable patient monitoring instrument.

3. The patient monitoring instrument of claim 1, wherein the contour further comprises means for guiding a collection tube connector into engagement with the first port.

4. The patient monitoring instrument of claim 1, further comprising a second opening in the case forming a second port, wherein the door covers the second port when the door is in the first position and uncovers the second port when the door is in the second position.

5. The patient monitoring instrument of claim 4, wherein the contour further comprises means for moving the door to the second position to expose both the first port and the second port.

6. The patient monitoring instrument of claim 1, wherein the contour further comprises a projection projecting from the outer surface of the door.

7. The patient monitoring instrument of claim 1, further comprising a collection tube connector adapted to meet with a luer receptacle, wherein the first port further comprises the luer receptacle adapted to engage the collection tube connector.

8. The patient monitoring instrument of claim 7, wherein the collection tube connector locks into engagement with the luer receptacle by turning the collection tube connector.

9. The patient monitoring instrument of claim 8, wherein the locked collection tube connector further comprises means for holding the door in its open position to expose a second port.

10. The patient monitoring instrument of claim 1 wherein the first port comprises a gas inlet port.

11. The patient monitoring instrument of claim 1 wherein the first port has a circular shape and the concave contour has an arcuate shape, wherein the radius of the concave contour is substantially the same as the radius of the first port, and further wherein the concave contour is substantially aligned with the first port when the door is in the second position.

12. The patient monitoring instrument of claim 1 wherein the first port comprises a fluid port.

13. The patient monitoring instrument of claim 1, further comprising a second opening in the case forming a second port, and wherein the second port is positioned and the door is structured so that the door covers the second port in the first position and uncovers the second port in the second position.

* * * * *